United States Patent [19]

Hlynsky et al.

[11] 3,963,751

[45] June 15, 1976

[54] CHLORINATION OF BUTADIENE SULFONE TO 3,3,4,4-TETRACHLOROTETRAHYDROTHIOPHENE-1,1-DIOXIDE

[75] Inventors: Alex Hlynsky, Mentor; Jan M. Griggs, Madison; Edmond R. Osgood, Mentor, all of Ohio

[73] Assignee: Diamond Shamrock Corporation, Cleveland, Ohio

[22] Filed: July 14, 1975

[21] Appl. No.: 595,531

[52] U.S. Cl. .......................... 260/332.1; 260/332.5
[51] Int. Cl.² ....................................... C07D 333/48
[58] Field of Search ............ 260/332.5, 332.8, 332.1

[56] References Cited

UNITED STATES PATENTS

| | | | |
|---|---|---|---|
| 2,922,826 | 1/1960 | Johnson et al. | 260/332.1 |
| 2,957,887 | 10/1960 | Berkey et al. | 260/332.1 |

*Primary Examiner*—James O. Thomas, Jr.
*Assistant Examiner*—A. Siegel
*Attorney, Agent, or Firm*—Helen P. Brush

[57] ABSTRACT

The biologically active compound, 3,3,4,4-tetrachlorotetrahydrothiophene-1,1-dioxide, is produced by the stepwise chlorination of butadiene sulfone, employing a free radical-generating compound as catalyst for the substitution chlorination stage of the reaction.

6 Claims, No Drawings

CHLORINATION OF BUTADIENE SULFONE TO 3,3,4,4-TETRACHLOROTETRAHYDROTHIOPHENE-1,1-DIOXIDE

BACKGROUND OF THE INVENTION 3,3,4,4-tetrachlorotetrahydrothiophene-1,1-dioxide has the structural formula:

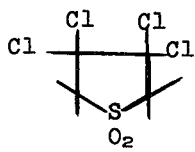

This compound, its preparation and its utility as a biologically active chemical are described in U.S. Pat. No. 2,957,887, issued Oct. 25, 1960, in the names of Reynold A. Berkey and Henry Bluestone. As conventionally practiced heretofore on a commercial scale, preparation of the compound has proceeded via a stepwise chlorination process, starting with butadiene sulfone, a cyclic unsaturated butadiene derivative. Butadiene sulfone is also designated chemically as 2,5-dihydrothiophene-1,1-dioxide. Initially, the cyclic starting material in solution in an inert solvent such as carbon tetrachloride is saturated by chlorination across the double bond, said addition chlorination being conducted at moderate temperatures. The resulting saturated 3,4-dichlorotetrahydrothiophene-1,1-dioxide product, likewise in solution, is chlorinated under moderate reaction pressure via photochlorination. That is to say, actinic light radiation is supplied to the reaction zone to serve as the chlorination catalyst.

However, the second-stage photochlorination step affords many disadvantages. In order to effect substitution chlorination to obtain 3,3,4,4-tetrachlorotetrahydrothiophene-1,1-dioxide in commercially feasible quantities, the sluggish, light-catalyzed chlorination reaction must usually be conducted for a time period of 50–60 hours. It must further be maintained under somewhat critical reaction conditions so that degradation of the product will be minimized during the long reaction time. Even so, degradation typically occurs with formation of polymeric derivatives as well as both trichloro- and dichlorotetrahydrothiophene-1,1-dioxide analogs which chlorinate to the pentachloro and hexachloro compounds. Thus, yields of the desired 3,3,4,4-tetrachlorotetrahydrothiophene-1,1-dioxide product oftentimes are less than commercially feasible. Chlorine reaction efficiencies for the overall chlorination reaction are poor, making byproduct hydrochloric acid disposal and/or extensive chlorine recovery equipment necessary in commercial operations. There has long been a need for a faster, more economical and commercially attractive method for converting butadiene sulfone to 3,3,4,4-tetrachlorotetrahydrothiophene-1,1-dioxide.

SUMMARY OF THE INVENTION

It has been found in accordance with the present invention that if the second stage of the aforesaid overall chlorination process, i.e., the substitution chlorination reaction, is conducted with the aid of a free radical-generating compound as catalyst rather than with a source of actinic light as presently used, substantially greater yields of tetrachlorotetrahydrothiophene-1,1-dioxide product may be obtained in significantly shorter reaction times then heretofore possible. Likewise, chlorination efficiencies usually are much greater than 50%. The specific free radical-generating compounds suitable for the chlorine substitution reaction are benzoyl peroxide and succinic acid peroxide.

DESCRIPTION OF THE PREFERRED EMBODIMENTS

As pointed out previously herein, the present invention relates only to improvements in the substitution chlorination step of the overall process involved in chlorinating butadiene sulfone. Neither the preparation of the starting material or of any intermediate chlorinated compounds resulting from addition chlorination mechanisms occurring during the reaction, nor such intermediate materials per se, constitute a part of this invention.

The initial addition or "dark" chlorination reaction herein is conducted in a suitable solvent such as carbon tetrachloride. It is a strongly exothermic reaction and proceeds smoothly at atmospheric pressure producing product in essentially quantitative yields. It may generally be completed in a time period of 4–8 hours, depending upon the rate of chlorine feed into the reactor. As the chlorine feed rate also governs the reaction temperature, chlorine is fed at a rate whereby the reaction temperature does not exceed about 50°C. In this way, the formation of undesirable products is substantially inhibited. For optimum control of the reaction temperature and efficiency, the chlorine feed rate ranges typically from about 15 to 18 lbs (6.8–8.2 kg)/hour.

As described previously, the substitution chlorination of the intermediate butadiene sulfone dichloride product obtained from the addition chlorination step is the novel reaction within the overall process of this invention. It is conducted with the aid of certain free radical-generating compounds introduced into the reaction mixture rather than through the use of actinic light as employed heretofore to supply the desired radiation for catalyzing formation of chlorine and free radicals and resulting substitution.

Surprisingly, the choice of the free radical-generating compound is especially critical for carrying out the chlorination reaction. Two organic peroxides have been found suitable as catalysts. Specifically, these are benzoyl peroxide which is an oil-soluble compound and succinic acid peroxide, a water-soluble material. In practice of this invention, higher chlorine efficiencies and product yields typically have been obtained with benzoyl peroxide which is presently preferred for use.

The substitution chlorination is likewise carried out in a suitable organic liquid medium such as carbon tetrachloride. In general, it may be conducted by admixing the reaction medium and the butadiene sulfone dichloride product from the first-stage chlorination, heating this mixture to the desired reaction temperature, and then feeding in chlorine and the catalyst at prescribed rates. In preferred methods of the invention, the addition chlorination is carried out and the substitution chlorination then conducted in the same reactor without isolating the intermediate product.

The temperature at which the substitution chlorination reaction is carried out ranges from about 75° to 90°C. This temperature range is found to be critical. At lower temperatures, substitution will not take place, or will proceed so slowly that any significant yields of the desired chlorinated product may not be obtained for several days. Conversely, at a temperature much higher than 90°C, the butadiene sulfone dichloride reactant may even be degraded significantly. Likewise, the substitution chlorination reaction preferably is carried out under slight positive pressure to assure optimum absorption and utilization of the gaseous chlorine in the reaction mixture. Generally, a pressure of 40–60 psig is sufficient for this purpose.

Although many organic peroxy compounds now known in the art will dissociate and effectively generate free radicals within the above-described temperature range, it has been found that the activity of only the two aforesaid organic peroxy compounds will not be inhibited by the strongly electronegative sulfone moiety of the reactant molecule and thus can suitably be used at catalyst for the substitution chlorination reaction of this invention. Generally, from about 5.0 to about 15.0%, preferably from about 7.0 to about 12.0% of these compounds may be employed, based on the weight of the butadiene sulfone starting material. For use, the catalyst compound is dissolved or dispersed in the same solvent as used in the reaction mixture, or in an organic liquid miscible therewith, such as chloroform. In practice, the catalyst solution or dispersion preferably is fed into the reactor at a prescribed rate throughout the reaction to provide for optimum uniformity of reaction, to inhibit degradation of the product, and likewise for safety.

As is illustrated in specific examples hereinafter, the overall process of this invention typically is carried out by initially chlorinating, with the exclusion of air, butadiene sulfone in a solvent such as carbon tetrachloride, over a time period of 4–8 hours and at a temperature no higher than 50°C, preferably at 30°–40°C. Upon completion of the first-stage chlorination step, the reaction mixture is then heated to the temperature required for the substitution chlorination reaction, while commencing addition of the catalyst solution to the reaction mixture at a prescribed rate. Typically the catalyst is fed at a rate of 0.5 to 1 pound (0.277–0.454 kg)/hour until chlorination is completed. When the temperature of the reaction mixture reaches the desired level, chlorine is fed into the reactor at a prescribed rate. This rate generally is 12–15 lbs (5.4–6.8 kg)/hour until chlorination is completed as determined by gas chromatographic analysis which indicates that substantially all of the trichlorotetrahydrothiophene-1,1-dioxide intermediate has been chlorinated.

Upon completion of the reaction, a portion of the solvent medium is removed in order to increase the concentration of product in the reaction mixture. The remaining reaction mass is then cooled and the solid product is isolated by centrifuging and drying.

By conducting the substitution chlorination reaction with the aid of an organic peroxy compound as catalyst rather than through the use of actinic radiation as heretofore used in the art, significant, i.e., greater than 70% of theoretical yields of 3,3,4,4-tetrachlorotetrahydrothiophene-1,1-dioxide may be obtained in reaction times of up to 30 hours. In contrast, from 40 to 60 hours reaction times are required to obtain significant yields via photochlorination.

By practice of the process of this invention, chlorine efficiencies are likewise significantly increased. These efficiencies are determined herein by conventional methods as e.g., by sampling and titrating off-gas for chlorine content, by determining the amount of hydrochloric acid in water from metered aliquots of off-gas and the like. A chlorine efficiency of greater than 80% may be realized in contrast to an average chlorine efficiency rating of 20–25% when conducting the substitution chlorination step with actinic radiation.

Utility of 3,3,4,4-tetrachlorotetrahydrothiophene-1,1-dioxide as a fungicide, bactericide, nematocide, and anti-fungal seed protectant has been set forth in the aforedescribed U.S. Pat. No. 2,957,887. The compound likewise is useful, either employed alone or in combination with other chemicals for controlling slime formation in industrial process waters or cooling water systems as described, e.g., in U.S. Pat. No. 3,862,322 and 3,865,724.

The process of this invention is further detailed in the following specific examples.

EXAMPLE 1

A. First Stage Chlorination

A jacketed, 100-gallon (378.5 liter), glass-lined reactor is charged with 142 lbs (1.20 lb. moles, 64.6 kg) of butadiene sulfone and 950 lbs (430.8 kg) carbon tetrachloride. The reactor is sealed and air is removed by nitrogen sweeping. With 9±1°C cooling water through the reactor jacket, chlorine is fed to the reactor at a rate of 15 lbs (6.8 kg)/hr. As chlorination proceeds, the temperature of the reaction mixture increases to 33°C, while the cooling water to the jacket is maintained at 9°C. After 90 lbs (39.8 kg) chlorine have been added, chlorination is completed (5-½ hours reaction time).

B. Second Stage Chlorination

The temperature of the jacket water is raised to 88°C, and the chlorine feed rate is adjusted to 13 lbs (5.9 kg)/hour. A nitrogen pressure of 40 psig is applied. A catalyst solution is prepared containing 227 g. of benzoyl peroxide per liter of chloroform. The catalyst feed pump is set to pump 1000ml of this solution per hour. When the temperature of the reaction mixture reaches 50°C, the catalyst feed pump is turned on and catalyst is fed continuously throughout the reaction. The reaction mixture is heated to 83°C and maintained at this temperature. The amount of catalyst used is 10.2%, by weight of the butadiene sulfone. The chlorination time for this stage of the reaction is 29 hours. The overall chlorine efficiency is 58.6%.

Upon completion of the reaction, 35 gallons (132.5 liters) of carbon tetrachloride is distilled from the reaction mixture, after which the remaining reaction mass is cooled to 10°C. The resulting thick slurry is pumped to a centrifuge and stripped further of the solvent medium. The wet cake product is then dried to obtain 73% of the theoretical yield of product which assays by Vapor Phase Chromatography 94% of the desired 3,3,4,4-tetrachlorotetrahydrothiophene-1,1-dioxide.

EXAMPLE 2

Following the procedure as outlined in Example 1 above, a mixture of 142 lbs. (64.4 kg) butadiene sulfone and 75 gallons (283.9 liters) of carbon tetrachloride is swept of air and chlorinated at atmospheric pressure, while being maintained at 30°C. Chlorine is fed at a rate of 11–12 lbs/hour. This stage of the reaction is completed in 8 hours.

The substitution chlorination is conducted for 21 hours at 83°C using a total of 10 lbs (4.54 kg) benzoyl peroxide (in chloroform solution), which quantity is equivalent to 7.0% by weight of the butadiene sulfone reactant. The calculated overall chlorine efficiency for the process of this Example is 81.6%.

The product is recovered and dried as described in Example 1. This product weighs 259 lbs (117.46 kg., 79.3% of the theoretical yield) and contains 95% of the desired 3,3,4,4-tetrachlorotetrahydrothiophene-1,1-dioxide.

EXAMPLE 3

The process as outlined in Example 2 is repeated. The addition chlorination reaction is conducted at a maximum temperature of 35°C for 5-½ hours. The substitution chlorination is conducted at a temperature of 83°–85°C for 18 hours, employing 11.2% total benzoyl peroxide catalyst, by weight of butadiene sulfone reactant. In this example, the catalyst in solution in chloroform is fed to the reactor at a rate of 1 lb (0.454 kg)/hour. The overall chlorine efficiency in this experiment is 43.5%.

EXAMPLE 4

The process as set forth in the previous Examples is repeated, conducting the addition chlorination at a maximum temperature of 40°C for 5-½ hours. The substitution chlorination is conducted at 83°C for 26-½ hours, feeding catalyst in solution in chloroform at a rate of one-half lb (0.227 kg)/hour until a total of 12 lbs (5.44 kg) catalyst has been pumped into the reaction. The total amount of catalyst used is 8.8%, by weight of the butadiene sulfone. The overall chlorine efficiency is determined to be 58.7%.

The finished product recovered in 77.7% yield has an assay of 96% 3,3,3,4-tetrachlorotetrahydrothiophene-1,1-dioxide.

EXAMPLE 5

A jacketed 100-gallon reactor as employed in the previous Examples is charged with 55 gallons (208.2 liters) carbon tetrachloride. The solvent medium is then heated to the boiling point to remove entrapped air. After the solvent is cooled, 135 lbs (1.14 lb. mole – 61.3 kg) of butadiene sulfone is added, the reactor is sealed and pressure tested for leaks. With 6°C cooling water through the reactor jacket, chlorine is fed to the reactor at a rate of 15 lbs (6.8kg)/hour. The addition chlorination reaction is completed in 5-¼ hours.

The reactor mixture is then slowly heated to 80°C under a pressure of 40 psig, while charging of a slurry containing 227 g. of succinic acid peroxide per liter of carbon tetrachloride is begun. The catalyst is fed at a rate of 227 g. catalyst/hour. The catalyst is fed until a total of 11 lbs (5.0 kg) of catalyst have been added (8.1% catalyst, by weight of the sulfone reactant). The total chlorination time is 30 hours with an average chlorine efficiency of 45%.

After distilling a portion of solvent from the reaction mixture and filtering the remaining reaction mass, 375 lbs (170.36 kg) of a wet cake is recovered which is found to contain 33% solvent. When dried, 251 lbs (114 kg) of product is obtained (76.8% yield). This product contains 90% of the desired 3,3,4,4-tetrachlorotetrahydrothiophene-1,1-dioxide.

Prior Art Photochlorination Process

For comparison purposes, into a jacketed, 100-gallon (378.5 liter), galss-lined reactor were charged 150 lbs (68.02 kg) butadiene sulfone and 60 gallons (227 liters) carbon tetrachloride. The reactor was sealed, and evacuated by nitrogen purging. The reaction mixture was cooled to 13°C. Chlorination was then conducted for 5-½ hours, during which time period, the temperature of the reaction mixture gradually increased to 31°C.

The reaction temperature was then raised to 50°C. The ultraviolet light was turned on and chlorine was introduced to the reaction. The reaction temperature was then increased to 80°C. The chlorination reaction was carried out while maintaining the reaction mixture at 79°–82°C under a nitrogen pressure of 40 psig. The reaction was completed in 42-½ hours, providing product in approximately 65% yield. The averaged chlorine efficiency for this phase of the reaction was only 23.5%.

We claim:

1. A process for preparing 3,3,4,4-tetrachlorotetrahydrothiophene-1,1-dioxide which comprises initially adding chlorine across the ethylenic double bond of butadiene sulfone by chlorinating said butadiene sulfone with chlorine in an inert solvent medium at a temperature no greater than 50°C; secondly chlorinating the obtained saturated 3,4-dichlorotetrahydrothiophene-1,1-dioxide with chlorine in the presence of an organic peroxy compound as the chlorination catalyst, said chlorination being conducted in an inert solvent medium, at a temperature of 75°–90°C and under a pressure of 40–60 psig, said organic peroxy compound being benzoyl peroxide or succinic acid peroxide; and finally recovering 3,3,4,4-tetrachlorotetrahydrothiophene-1,1-dioxide product in greater than 70% yield.

2. The process of claim 1 wherein the organic peroxy catalyst is benzoyl peroxide.

3. The process of claim 1 wherein the organic peroxy catalyst is succinic acid peroxide.

4. The process of claim 1 wherein the inert solvent medium employed for both the first and second chlorination reactions is carbon tetrachloride.

5. The process of claim 1 wherein the organic peroxy catalyst is used in an amount ranging from 5.0% to about 15.0%, based on the weight of the butadiene sulfone reactant.

6. The process of claim 1 wherein the second chlorination reaction is conducted for a time period of 15–30 hours.

* * * * *